United States Patent [19]

Lake

[11] 4,445,508

[45] May 1, 1984

[54] NASAL PROTECTIVE METHOD AND DEVICE

[76] Inventor: Norman M. Lake, 1705 Newport Dr., Lancaster, Pa. 17602

[21] Appl. No.: 385,789

[22] Filed: Jun. 7, 1982

Related U.S. Application Data

[63] Continuation of Ser. No. 183,214, Sep. 2, 1980, abandoned.

[51] Int. Cl.$^3$ ............................................. A61M 16/00
[52] U.S. Cl. ................................. 128/201.18; 128/346
[58] Field of Search ...................... 128/201.18, 206.11, 128/203.22, 346

[56] References Cited

U.S. PATENT DOCUMENTS

| | | | |
|---|---|---|---|
| 1,802,275 | 4/1931 | Roche | 128/206.11 |
| 4,033,342 | 7/1977 | Lake | 128/201.18 |
| 4,221,217 | 9/1980 | Amezcua | 128/206.11 |

Primary Examiner—Henry J. Recla

[57] ABSTRACT

Protective method and apparatus for the nasal passages comprising a U-shaped wire spring each leg of which being embedded within, and held by friction, an ellipsoidal-like nub for closing the nose by pressing it on its sides and to raise the temperature of the nasal passages.

1 Claim, 3 Drawing Figures

FIG. 1
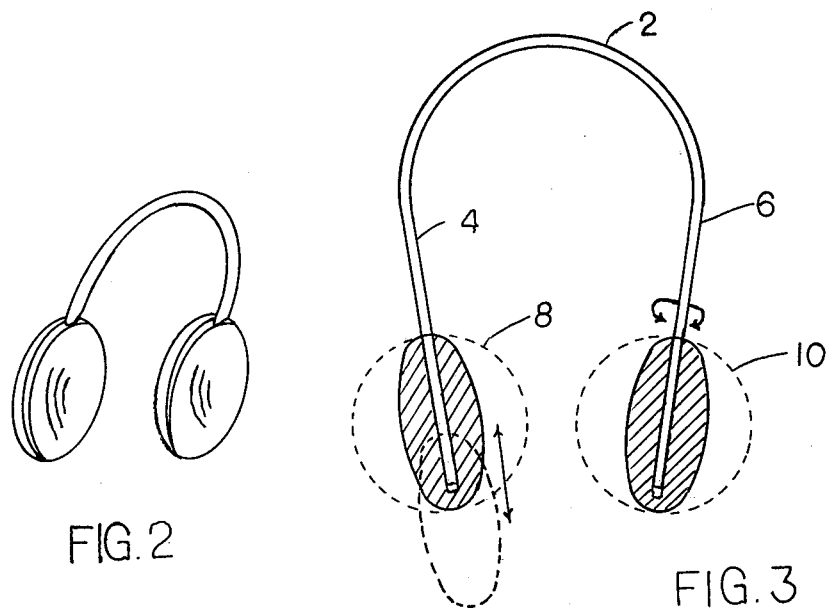
FIG. 2
FIG. 3

NASAL PROTECTIVE METHOD AND DEVICE

CROSS-REFERENCE TO RELATED APPLICATION

This is a continuation, of application Ser. No. 183,214, filed Sept. 2, 1980 and now abandoned.

This application is an improvement over that of Applicant's application Ser. No. 610,655, filed Sept. 5, 1975, entitled "Nasal Protective Splint" and issued as U.S. Pat. No. 4,033,342 on July 5, 1977.

BACKGROUND OF THE INVENTION

1. Field of the Invention

This invention relates to an improvement in nasal protectors for the protection of the mucous membranes of the nasal passages.

2. Description of the Prior Art

The prior art teaches the use of numerous nasal protective devices, but does not teach the use of a device that closes off the nasal passages for the purpose of creating in the nose nasal passage a condition substantially equivalent to inflammation, the natural defensive reaction to irritation.

U.S. Pat. No. 2,317,236 is typical of the prior art wherein a nose clip closes the nasal passages but under conditions that will not develop the natural defensive reaction of inflammation.

SUMMARY OF THE INVENTION

The apparatus of the invention is a nasal splint having a U-shaped wire spring with an ellipsoidal-like shaped nub on each leg of the spring. Each nub is rotationally and longitudinally adjustable with regard to each leg of the spring to adjust the splint to human noses of different sizes.

The method of using the inventive device above requires that the splint be positioned on the nose to close off the nasal passages and exert a firm pressure on the septum for a period of 30 minutes or more causing the nasal temperature to rise sufficiently to create a condition in the nose substantially equivalent to inflammation, the natural defensive reaction to irritation but without the pain and suffering of inflamed and swollen membranes.

BRIEF DESCRIPTION OF THE DRAWING

FIG. 1 illustrates the nasal splint in use.

FIG. 2 is a perspective view of the nasal splint, and

FIG. 3 is a cross-sectional view of the ends of the nasal splint.

DESCRIPTION OF THE PREFERRED EMBODIMENTS

This invention relates to an improvement in nasal protectors and has for its object the protection of the mucous membranes of the nasal passages. To this end inhalation of airborne irritants entering the nose are trapped and minimized; reactions to a stimulus (which are manifested by sneezing) are inhibited, and "inflammation" (the natural defensive reaction to irritation) is simulated.

Toward this objective (1) the nose of the human is closed to a degree sufficient to trap and minimize inhalation of airborne irritants entering the nose but insufficient to block breathing and watery secretions therefrom, (2) the nose is wholly closed off by exerting a firm pressure on its sides for 30 minutes or more (during which time forceful attempts to inhale through nose should be exercised) to inhibit the explosive actions of sneezing by control of voluntary muscles of the nose, and (3) the nasal temperature is caused to rise sufficient to create a condition substantially equivalent to inflammation (inflamed and swollen membranes), the natural defensive mechanism of the nose. Thus precluding or abating the inflammatory process whereby the evils therefrom are arrested or alleviated.

The means employed for implementing this invention is a small improved nasal splint comprising a resilient and adjustable music wire spring 2 (ranging in diameter 0.030 of an inch) each leg 4 and 6 of which is embedded along the central axis holding by friction an ellipsoidal-like nub 8 and 10, preferably of polyethylene, having a certain elastic quality to permit adjustment of each nub along and around each leg of the spring, thus adapting the nasal splint to conform with comfort to the size and shape of the nose.

This invention has two unique improvements over that of my previous U.S. Pat. No. 4,033,342 issued July 5, 1977. In that patent, each leg of the U-shaped spring was rigidly embedded in a different one of the nubs, whereas in this improved invention, each nub is held to a different leg of the spring only by friction but with sufficient gripping power thus providing for easy adjustment, more comfort to the wearer and adaptability to conform with the shape and size of nose.

The second and major improvement in this invention is the period of time of closing off the nasal passages. In my previous U.S. Pat. No. 4,033,342, the time period of closing the nose was only two or three minutes for the purpose of inhibiting sneezing. Whereas this improved invention requires closing off the nose for a period of 30 minutes or more causing a rise in nasal temperature and thus creating a temporary condition in the nose substantially equivalent to inflammation, the natural defensive mechanism of the nose.

During the fall, winter and spring seasons particularly, the nasal mucous membranes of the individual are subjected to attack by countless airborne irritants which are constantly being breathed into the nose, some of which are often infectious. Many of these agents, after entering the nose, are conveyed by the mucous blanket back to the throat where they are swallowed and rendered harmless. But, unfortunately, some succeed in escaping this movement to the throat and, instead, land in and attack the membranes. Irritation then begins and evils generate and develop. When this condition is reached, the individual soon succumbs to the explosive actions of sneezing—and as sneezing is well known to irritate the nasal mucous membranes—the problem then becomes compounded, causing a rapid development of the inflammatory process which results in nasal blockage and in other complications. When an irritating agent attacks the nasal mucosa, irritation therefrom ensues. Two things then promptly occur, (1) the small vessels of the nasal membranes dilate and watery secretions therefrom are increased, and (2) nature reacts to this irritation by sneezing which appears to be nature's way of removing the agent that is causing the irritation. If the causative agent is non-infectious, sneezing will often dislodge it and the secretions, which are part of nature's defense cycle, can wash it back in the throat to be swallowed. However, the non-infectious invader can often become so entrenched in the nasal mucosa that sneezing will fail to dislodge it, and along with its continued irritation coupled with that from sneezing, complications can surely be expected to follow. If, on the other hand, the irritation is being caused by an infectious agent, a different situation develops, that is, the agent has succeeded in gaining entrance to a living cell from which it gains protection from being dislodged by sneezing. So here again, an invader is inflicting irritation and setting the stage for complications to follow, which in this case are perhaps more serious. In both of these cases, irritation of the nasal passages causes the inflammatory process to develop, resulting in nasal blockage and inflamed membranes, but when the inflammatory process is caused by an infectious agent, favorable conditions are thereby created under which this infectious agent may multiply and produce results that are injurious.

An object of this invention first of all is to (1) reduce to a minimum the inhalation of irritating agents entering the nose, (2) inhibit the reactions of sneezing to these irritants which escape the mucous blanket and initiate irritation in the nasal mucosa, and (3) simulate inflammation, the natural defensive reaction to irritation.

From my own observations and clinical studies by research scientists, the average nasal disorder generally called a common head cold or hay fever is diagnosed usually only by guess. But one thing is quite certain, the symptoms are virtually the same. The disorder is generally sensed by repeated spells of sneezing, water dropping from nose and, at times, a slight scratchy feeling in the throat. During the first 36 to 48 hours, all the usual painful symptoms are developing until the peak of nasal obstruction is finally reached and then something significant happens. That is, all symptoms are brought to a halt and begin shortly thereafter to subside progressively toward zero, but it takes five or more days for all symptoms to disappear.

What brought about this phenomenon? It cannot be credited to antibodies because more than one clinical study has discovered that the antibodies present in such cases are not due to the infecting virus. So the overcoming of such illnesses is left in the hands of mother nature to develop inflammation (heat and swelling) as the last resort to end such disorders. And those two vital conditions, heat (increased nasal temperature) and swelling (nasal blockage), provide the defensive action which ultimately overcomes nasal disorders such as hay fever and common head colds. Thus, when the nose is closed with this nasal splint, nasal blockage occurs and the nasal temperature rises, thereby simulating or mimicking inflammation, the natural defensive mechanism, of the nose.

In brief, this improved method of prolonging the time of closing off the nasal passages is precisely the difference between failure and success in preventing the inflammatory process and arresting nasal disorders. Hence, when repeated spells of sneezing occur, the nasal splint should be adjusted and applied to close off the nasal passages and to exert a firm pressure on the nasal septum (position 1, FIG. 1); and while holding this position for a period of 30 minutes or more, forceful attempts to inhale through the nose should be exercised. At the end of the said period, adjust the splint to a degree only sufficient to breath comfortably through the nose, yet retain a degree of constriction in the nasal passages (position 1', FIG. 1). In this adjusted position of the nasal splint, it will trap and minimize inhalation of irritants entering the nose and enhance its filtering system. It can be worn in this position as long as desired with safety and little or no discomfort.

It should be noted that when the nasal mucous membranes are under attack, watery secretions of the nose occur. By actual experience, I have discovered that blotting these secretions rather than blowing the nose has proved most helpful toward achieving the objective of the invention. Furthermore, use of this nasal splint will operate as a deterrent to nose blowing.

This invention resides not merely in using a nasal clip, but in making a nasal protective splint adaptable for a new and inventive use. The prime object of the invention is to fulfill a health need long desired but never attained which fact is manifested by its absence of availability for public benefit. My invention is novel since it is out of the ordinary and unobvious because it is insufficiently evident as to arrest attention.

The nasal splint has striking properties over conventional nasal protective devices, namely, (1) practicability (more acceptable for public use); (2) less unsightly to wear; (3) comfortable to wear; (4) no health hazard; (5) manufacturing costs will be at a minimum since it comprises only two simple parts; (6) a lower price level can be created by making volume production easier.

In two tests to determine rise in temperature in the nasal passages, the following temperature/times were recorded:

| Test 1 | |
|---|---|
| Time Nose Closed Off (mins.) | Temperature in Nasal Passage |
| 0 | 33.5° C. (92.3° F.) |
| 5 | 35.8° C. (96.4° F.) |
| 10 | 36.4° C. (97.5° F.) |
| 15 | 36.5° C. (97.7° F.) |
| 20 | 36.5° C. (97.7° F.) |
| 25 | 36.7° C. (98.06° F.) |
| 30 | 36.7° C. (98.06° F.) |

| Test 2 | |
|---|---|
| Time Nose Closed Off (mins.) | Temperature in Nasal Passage |
| 0 | 33° C. (91.4° F.) |
| 5 | 35.8° C. (96.4° F.) |
| 10 | 36.4° C. (97.5° F.) |
| 15 | 36.6° C. (97.8° F.) |
| 20 | 36.6° C. (97.8° F.) |

During both tests, the temperature in the mouth was 97.4° F. The average normal temperature in the nose is 33° C. (91.4° F.). The higher temperatures are in the range of inflamed nasal mucous membranes, a vital condition of inflammation.

Having thus described my invention, what I claim as new and desire to secure by Letters Patent is:

1. A new process of employing an improved nasal splint for helping the human nose maintain its mucous membranes in good condition, said splint comprising a U-shaped wire spring for straddling the nose and having two nubs each of ellipsoidal-like shape of circular outline with two convex side faces, each leg of the U-shaped spring being embedded in the longitudinal axis of a different one of the nubs and employing the improvement of each leg holding the nubs only by friction to allow the same to be rotatable and slidable on the legs of the spring, and said process comprising locating the splint such that the spring of the splint presses the nubs in on the sides of the nose in an appropriate area defined by the portion above the alae and by the upper portion of the alae, this being done to the extent of closing off the nasal passages by exerting a firm pressure on the septum and wherein the improvement comprising closing off the nasal passages for a period of 30 minutes or more thereby causing the nasal temperature to increase from its normal 91° F. to about 98° F. then relocating said splint such that its spring presses the nubs in on the sides of the nose in the area defined by the portion just above the alae, this being done to a degree sufficient to trap and minimize inhalation of airborne irritants entering the nose but insufficient to block breathing and watery secretions therefrom thus enhancing the nasal filtering system and helping the nose protect against the numerous irritants breathed into the nose during certain seasons of the year.

* * * * *